United States Patent [19]

Holzner et al.

[11] Patent Number: 5,641,888
[45] Date of Patent: Jun. 24, 1997

[54] SYNTHESIS OF AN O,O'-DIESTERS OF THIOPHOSPHORIC ACID, AN O-ESTER OF THIOPHOSPHONIC ACID, OR A THIOPHOSPHINIC ACID

[75] Inventors: Christoph Holzner; Ottfried Schlak, both of Köln; Rosemarie Grizan; Johannes Jezierski, both of Leverkusen, all of Germany

[73] Assignee: Bayer Aktiengesellschaft, Leverkusen, Germany

[21] Appl. No.: 588,479

[22] Filed: Jan. 18, 1996

[30] Foreign Application Priority Data

Jan. 25, 1995 [DE] Germany ............ 195 02 197.5

[51] Int. Cl.$^6$ ............... C07F 9/40; C07F 9/30; C07F 9/165
[52] U.S. Cl. .................... 558/123; 562/8
[58] Field of Search .................. 558/123; 562/8

[56] References Cited

U.S. PATENT DOCUMENTS

| | | | |
|---|---|---|---|
| 2,647,140 | 7/1953 | Jonas | 558/123 |
| 3,984,448 | 10/1976 | Lippsmeier | 558/123 X |
| 5,200,099 | 4/1993 | Cardis | 558/123 X |
| 5,210,261 | 5/1993 | James et al. | 558/123 |

OTHER PUBLICATIONS

Methoden der Organischem Chemie (Houben–Weyl), 4th edition, vol. 12/2, pp. 602–604, 268, 560 (1964).

G. Cote, et al., Reviews in Inorganic Chemistry, vol. 10, Nos. 1–3, pp. 121–144, (1989).

K.C. Sole, et al., Hydrometallurgy, vol. 30, pp. 345–365, (1992).

Chemical Abstracts, vol. 117, No. 12, abstract No. 115533c, abstract of Tohoku Kogyo Gijutsu Shikensho Hokoku, vol. 25, pp. 47–51, (1992).

Chemical Abstracts, vol. 89, No. 25, abstract No. 215499t, abstract of Izv. Sib. Otd. Akad. Nauk SSSR, Ser. Khim. Nauk, (4), pp. 146–147, (1978).

Chemical Abstracts, vol. 119, No. 3, abstract No. 28247k, abstract of Huaxue Shiji, vol. 15 (1), pp. 41–42, (1993).

Chemical Abstracts, vol. 116, No. 15, abstract No. 151877f, abstract of Phosphorus, Sulfur, and Silicon, vol. 63, pp. 315–322, (1991).

H. Zinke, et al., Phosphorus, Sulfur, and Silicon, vol. 63, pp. 315–322, (1991).

Liu, et al., Huaxue Shiji, vol. 15, No. 1, pp. 41–42, (1993).

Y. Wakui, et al., Tohoku Kogyo Gijutsu Shikensho Hokoku, vol. 25, pp. 47–51, (1992).

*Primary Examiner*—Johann Richter
*Assistant Examiner*—Michael G. Ambrose
*Attorney, Agent, or Firm*—Sprung Horn Kramer & Woods

[57] ABSTRACT

Preparing O,O'-diesters of thiophosphoric acid, O-monoesters of thiophosphonic acid or thiophosphinic acids and their salts, from diesters of phosphorous acid, monoesters of phosphorous acids or phosphinous acids and sulphur in the presence of an aqueous solution of an auxiliary base. The solutions can be used in further syntheses or as extraction agent for cations.

11 Claims, No Drawings

SYNTHESIS OF AN O,O' -DIESTERS OF THIOPHOSPHORIC ACID, AN O-ESTER OF THIOPHOSPHONIC ACID, OR A THIOPHOSPHINIC ACID

The present invention relates to a process for preparing O,O'-diesters of thiophosphoric acid, O-monoesters of thiophosphonic acid or thiophosphinic acids and their salts, from diesters of phosphorous acid, monoesters of phosphonous acid or phosphinous acids and sulphur, and use of the aqueous salt solutions thereby prepared.

O,O'-diesters of the general formula (RO)(R'O)PS(OH) are used in industry for extracting heavy metal ions from aqueous solutions (G. Cote, D. Bauer; Reviews in Inorganic Chemistry, vol. 10. nos 1–3, (1989), 121–144). An outstanding property of diesters of thiophosphoric acid is their particularly high extraction capacity for thiophilic metal ions such as e.g. $Ag^+$ (Y. Wakui, H. Matsunaga, T. M. Suzuki; Tohoko Kogyo gijutsu shikensho hokoku, Sendai (Japan), 25 (1992), 47–51; Chemical Abstract 117 (12): 115533 c). Chemically applied O-monoesters of thiophosphinic acid of the general formula (RO)R'PS(OH) and thiophosphinic acids of the general formula RR'PS(OH) may be used for Co/Ni separation (K. C. Sole, J. B. Hiskey; Hydrometallurgy, 30, (1992), 345–365).

O,O'-diesters of thiophosphoric acid are prepared, according to the prior art, from the corresponding diesters of phosphorous acid (R'O)(RO)PH(O) by reaction with sulphur in the presence of an anhydrous auxiliary base (Methoden der organischen Chemie (Houben-Weyl), 4th edition, (1964), vol 12/2, p. 602–604). In accordance with the following equation, according to which the auxiliary base abstracts a proton from the PH(O) group,

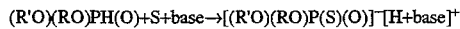

(R'O)(RO)PH(O)+S+base→[(R'O)(RO)P(S)(O)]⁻[H+base]⁺ a salt of the O,O'-diester of thiophosphoric acid is initially produced. This salt then has to be retained in solution during the reaction, since the salt precipitating during reaction would hinder dissolution of the sulphur suspended in the reaction mixture and thus hinder complete reaction.

This problem is solved by adding an organic solvent together with the anhydrous auxiliary base. Thus, Liu et al. use 240 ml of benzene as solvent in 117 ml of di(2-ethylhexyl)phosphite to produce O,O'-di(2-ethylhexyl) thiophosphate. Gaseous ammonia is used as the auxiliary base (X. Liu, Y. Ge, Y. Song; Huaxue Shiji, vol. 15, (1993), pages 41 and 56 Chemical Abstract 119 (3): 28247 k). This same combination of solvent and auxiliary base is described by O. M. Frid, S. N. Ryabchenko, I. S. Levin in Izvestija Sibirskogo Otdelenija Akademii Nauk SS/Serija chimiceskich (Novosibirsk), vol. 4. (1978), pages 146 to 147; Chemical Abstract 89 (25): 215 499 t).

H. Zinke and R. Schumacher use a total of 1.2 l of isopropanol as solvent to convert 582 g of O,O'-diisopropyl phosphite with sulphur and gaseous ammonia (H. Zinke, R. Schumacher; Phosphorus, Sulfur and Silicon, vol. 63 (1991), pages 315 to 322; Chemical Abstract 116 (15): 151877 f).

A general method of preparation of O,O'-diesters of thiophosphoric acid uses the corresponding sodium or potassium alcoholate as auxiliary base and diethyl ether as organic solvent (Methoden der organischen Chemie (Houben-Weyl), 4th edition, (1964), vol. 12/2, page 602).

The analogous production of 0-monoesters of thiophosphonic acid from O-monoesters of phosphonous acid and of thiophosphinic acids from phosphinous acids is also described, using organic solvents and anhydrous auxiliary bases (Methoden der organischen Chemie (Houben-Weyl), 4th edition, (1964), vol. 12/2, pages 560 and 268).

The use of anhydrous auxiliary bases and organic solvents for the preparation of O,O'-diesters of thiophosphoric acid, however, has a few disadvantages:

Thus, anhydrous bases are either very expensive or very complicated to prepare (such as the Na or K salts of the alcohol appropriate to the particular ester) or complicated to handle (such as gaseous ammonia).

Again, organic solvents lower the volume yield of the process. In addition they have to be separated from the desired product after reaction because they interfere with use of the product, especially during the liquid/liquid extractions hereinbefore mentioned. The solvent is removed by distillation, which leads on the one hand to higher production costs and on the other hand to increased thermal strain on the thio compound, which may decompose to a small extent during distillation.

Despite these disadvantages, the use of anhydrous bases and organic solvents has hitherto been adhered to, from fear that the use of water-containing bases or of water as solvent would lead to hydrolysis of the esters.

The object of the present invention is, therefore, to provide a process for preparing O,O'-diesters of thiophosphoric acid which produces the desired product in high purity and with high space-time yields while using reasonably priced and easily handled auxiliary bases without the use of organic solvents.

This object is achieved by the process according to the invention. Surprisingly, it was found that the reaction with sulphur and base proceeds far more rapidly than concurrent hydrolysis of the ester so that the exclusion of water is completely pointless and only leads to unnecessary complications.

The invention provides a process for preparing O,O'-diesters of thiophosphoric acid, O-monoesters of thiophosphonic acid or thiophosphinic acids of the general formula (R)(R')PS(OH) and their salts of the general formula (R)(R')PS(OZ) from the corresponding diesters of phosphorous acid, monoesters of phosphonous acid or phosphinous acids of the general formula (R)(R')PH(O) and sulphur, wherein R and R' represent identical or different alkyl, alkenyl, cycloalkyl or aryl groups with 1 to 18 carbon atoms, whose hydrogen atoms may be replaced completely or partly by halogen atoms or by neutral or basic groups, or represent $R_1O$ or $R_1'O$ groups in which $R_1$ and $R_1'$ have the same meaning as R and R', and Z represents alkali metal ions, alkaline earth metal ions, protonated, nitrogen-containing inorganic bases or organic derivatives of these nitrogen-containing, protonated bases, which is characterized in that the reaction is performed in the presence of an aqueous solution of an auxiliary base.

The process according to the invention can be utilized to prepare O,O'-diesters of thiophosphoric acid or their salts from diesters of phosphorous acid, of O-monoesters of thiophosphonic acid or their salts from monoesters of phosphonous acid and to synthesize thiophosphinic acids or their salts from phosphinous acids by adding sulphur and using aqueous auxiliary bases. The following reaction schemes clarify the course of the reactions and the chemical structure of the particular starting materials and products.

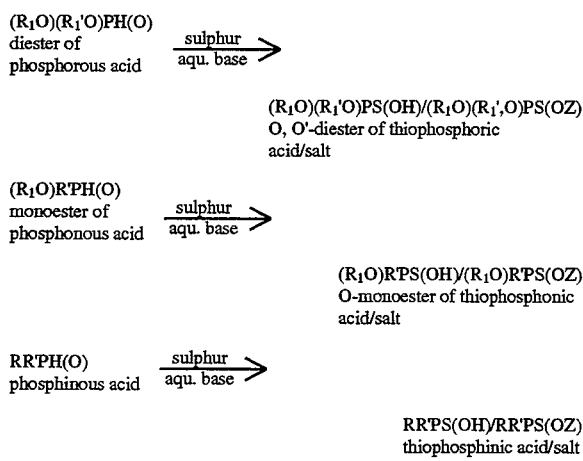

The groups R, R', $R_1$ and $R_1'$ preferably represent identical or different alkyl, alkenyl, cycloalkyl or aryl groups with 1 to 18 carbon atoms. The hydrogen atoms in these alkyl, alkenyl, cycloalkyl or aryl groups may preferably be replaced partly or completely by other atoms such as, for example, halogen atoms, or by neutral or basic functional groups such as, for example, hydroxy, alkoxy, carbalkoxy or amino groups. Particularly preferred groups as R, R', $R_1$ and $R_1'$ are 2-ethylhexyl, n-butyl, n-octyl and 2,4,4-trimethylpentyl groups.

The group Z preferably represents an alkali metal (in particular sodium and potassium), an alkaline earth metal (in particular magnesium and calcium), a protonated, nitrogen-containing inorganic base (in particular $NH_4^+$ and $H_2N$—$NH_3^+$) or an organic derivative of these nitrogen-containing protonated bases (in particular $NR^2R^3R^4H^+$ and $R^2R^3C=NR^4H^+$ and $R^2R^3C=N$—$NR^4R^5H^+$ where $R^2$, $R^3$, $R^4$ and $R^5$ are identical or different alkyl, cycloalkyl or aryl groups with 1–10 carbon atoms or hydrogen atoms).

Preferred auxiliary bases are solutions of alkali metal or alkaline earth metal hydroxides or aqueous solutions of basic nitrogen compounds such as, for example, ammonia, hydrazine, amines, imines or hydrazones.

The auxiliary base is preferably used as a 5–95% strength, in particular 5–60% strength, solution, wherein the most concentrated solutions possible are particularly preferred. Depending on the type of base used, the preferred concentration can vary over a very wide range. Ammonia water, for example, can be obtained only at a maximum concentration of 34% at room temperature and atmospheric pressure but, in contrast, trimethylamine solution can be obtained at a concentration of 45%. Dimethylamine has unlimited miscibility with water. Organic bases which have a miscibility gap with water, such as, for example, triethylamine, may also be used as water-saturated bases, i.e. as a solution of water in the base.

After reaction, the auxiliary base preferably remains in the prepared product in the form of its conjugated acid and provides the positive counterion to the anion of the thioacid prepared. The preferred choice of auxiliary base thus effectively depends on which salt of the thioacid it is intended to prepare. If a specific amino salt of the thioacid is desired, then this specific amine is accordingly selected as the auxiliary base.

If, on the other hand, the salt is only an intermediate for preparation of the free acid, then an aqueous ammonia solution or a trimethylamine solution is preferred as auxiliary base. The free acids are prepared simply by the subsequent addition of inorganic acids to the reaction mixture.

Sulphur and the auxiliary base are preferably used in excess with respect to the phosphorus component.

The molar ratio of starting materials should be selected in particular so that 1 to 2 mols of sulphur and 1 to 1.5 mols of base are used per mol of phosphorus compound.

An excess of sulphur is preferred because then the very last remnants of the phosphorus compound react rapidly and completely to give the desired product. The excess sulphur can be filtered off after reaction and used again in the next batch without further purification.

The favorable effect of the preferred excess of base can be explained in that all PH(O)-containing phosphorus compounds in practice also contain impurities of more strongly acidic compounds with P(O)(OH) groups. These impurities can neutralize some of the auxiliary base used and thus withdraw it from the actual reaction.

Surprisingly, the water contained in the aqueous auxiliary base does not have a negative effect on the reaction although, in particular in the case of diesters of phosphorous acid which have two hydrolyzable alkoxy groups on the P atom, it would have been expected that, in the presence of water, hydrolysis would occur with formation of the PO(OH) compounds mentioned above. This proves that the reaction with sulphur and auxiliary base apparently proceeds more rapidly than the concurrent hydrolysis reaction.

Under suitable reaction conditions, which depend on the starting compounds used, the reaction can be performed in such a way that hydrolysis plays virtually no part. Suitable reaction conditions mean that it is preferred that sulphur and auxiliary base are used in excess, that the auxiliary base is used in as concentrated a solution as possible and is added to the mixture of P compound and sulphur in as short a time as possible or, conversely, that the P compound is added to a mixture of aqueous auxiliary base and sulphur.

The temperature during reaction is preferably between about 0° and 60° C. Since the desired reaction is strongly exothermic, this temperature range is maintained by cooling.

Not only does the water contained in the auxiliary base used not have a negative effect of the desired reaction, it also has an additional positive effect. That is, it acts as solvent for the salt of the thioacid being produced and therefore replaces the organic solvent required according to the prior art. Due to its high degree of polarity, quite small amounts of water can replace much larger volumes of non-polar organic solvents.

A further advantage of the process according to the invention is the saving in reaction volume which is equivalent to an increase in volume yield. In addition, water does not interfere in the most important application of thioacids, liquid/liquid extraction. A reaction mixture obtained from O,O'-di(2-ethylhexyl) phosphite, sulphur and ammonia water can be used directly, for example, for liquid/liquid extraction, after filtering off the excess sulphur. In addition the reaction mixture, when the sulphur has been removed, can also be mixed with a water-immiscible diluent such as an aliphatic or aromatic hydrocarbon or a long-chain aliphatic alcohol, such as isodecanol, or mixtures thereof. The mixture obtained in this way acts as an extraction agent for metal ions when placed in contact with an aqueous metal salt solution.

If the water is to be removed after reaction, this expediently occurs during conversion of the salt into the free acid. Excess aqueous sulphuric acid is simply added to the reaction mixture, for instance. The di(2-ethylhexyl) thiophosphoric acid thereby produced, for example, separates as the organic phase. All the water collects in the aqueous sulphuric acid phase and can be removed by phase separation.

The water may thus, if so desired, be removed by simple phase separation at room temperature.

Since there is no solvent distillation stage, as has been involved in the processes known hitherto, there is no thermal strain placed on the free thioacid. This means that the product purity also increases considerably. Furthermore, the lack of a distillation stage leads to savings in time and costs.

A further additional advantage of the process according to the invention is the low cost and ease of handling of the aqueous bases used. Thus, for example, a 25% strength ammonia solution is simpler and less hazardous to dispense than liquid or gaseous ammonia.

The following illustrative examples are intended to explain the invention in more detail.

EXAMPLE 1

Preparation of ammonium O,O'-diethyl thiophosphate 414 g (3 mols) of O,O'-diethyl phosphite and 192 g (6 mols) of milled sulphur are initially placed in a reaction flask. 255.5 g (3.75 mols) of 25% strength ammonia water are added dropwise over the course of 15 minutes, with stirring and the use of an ice bath. The temperature of the mixture is <40° C. Stirring is continued for 2.5 hours and excess sulphur is filtered off. $^{31}$P NMR analysis of the filtrate shows the presence of the desired ammonium O,O'-diethyl thiophosphate. The yield is 92% of theoretical.

EXAMPLE 2

Preparation of O,O'-dibutyl thiophosphoric acid 583 g (3 mols) of O,O'-dibutyl phosphite and 192 g (6 mols) of milled sulphur are initially introduced into a reaction flask. 225 g (3.3 mols) of 25% strength ammonia water are added dropwise over the course of 25 minutes, with stirring and the use of an ice bath. The temperature of the reaction mixture is 36°–40° C. Stirring is continued at this temperature for 2.5 hours after addition of the ammonia. After the addition of 125 ml of water, the sulphur is filtered off. The filtrate is stirred for 15 minutes with 674 g (3.3 mols) of 48% strength sulphuric acid. After phase separation, O,O'-dibutyl thiophosphoric acid separates, as the less dense phase, from the aqueous sulphuric acid/ammonium hydrogen sulphate solution. During two subsequent washing procedures using 500 ml of water each time, however, the product separates as the more dense phase. The product can be heated at 60° C under reduced pressure (20 mbar) for 25 minutes, following the last phase separation, in order to remove residual water. The $^{31}$P NMR spectrum of the yellow, clear liquid shows the presence of the desired O,O'-dibutyl thiophosphoric acid. The yield after removal of water is 95% of theoretical.

EXAMPLE 3

Preparation of trimethylammonium O,O'-di(2-ethylhexyl) thiophosphate 278 g (0.908 mol) of O,O'-di(2-ethylhexyl)phosphite and 29.1 g (0.908 mol) of sulphur are initially introduced into a reaction flask. 131 g (1 mol) of 45% strength aqueous trimethylamine solution are added dropwise to the suspension over the course of 40 minutes, with stirring and cooling. The temperature during addition of the amine is between 35° and 40° C. After stirring for another 3 hours at the same temperature, any undissolved residual sulphur is filtered off. A $^{31}$P NMR spectrum of the filtrate shows the presence of the desired trimethylammonium O,O'-di(2-ethylhexyl) thiophosphate. The yield is 98% of theoretical.

EXAMPLE 4

Preparation of O,O'-di(2-ethylhexyl)thiophosphoric acid 368 g (1.2 mols) of O,O'-di(2-ethylhexyl)phosphite and 58 g (1.8 mols) of sulphur are initially introduced into a reaction flask. 102 g (1.5 mol)s of 25% strength ammonia water are added to the suspension over the course of 1 hour, with stirring and cooling. The temperature of the reaction mixture during addition of ammonia is 35°–43° C. Stirring is continued at this temperature for another 3 hours after addition of the ammonia. Then 337 g (1.65 mols) of 48% strength sulphuric acid are added. After filtering off excess sulphur, the phases are separated. O,O'-di(2-ethylhexyl) thiophosphoric acid separates as the less dense phase. This is washed twice with 4.8% strength sulphuric acid. Residual aqueous phase, which causes cloudiness in the organic phase, is removed by filtration or by evaporating under vacuum. The $^{31}$P NMR spectrum of the yellow, clear liquid shows the presence of the desired O,O'-di(2-ethylhexyl) thiophosphoric acid. The yield is 96% of theoretical.

It will be understood that the specification and examples are illustrative but not limitative of the present invention and that other embodiments within the spirit and scope of the invention will suggest themselves to those skilled in the art.

We claim:

1. In the preparation of an O,O'-diester of thiophosphoric acid, an O-monoester of thiophosphonic acid or a thiophosphinic acid of the formula (R)(R')PS(OH)

or a salt thereof of the formula (R)(R')PS(OZ)

wherein

R and R' each independently is an alkyl, alkenyl, cycloalkyl or aryl group with 1 to 18 carbon atoms, whose hydrogen atoms may be replaced completely or partly by halogen atoms or by neutral or basic groups; or $R_1O$ or $R_1'O$ group in which R' and $R_1'$ each independently has the same meaning as R and R', and Z is an alkali metal ion, alkaline earth metal ion, protonated nitrogen-containing inorganic base or organic derivative of a nitrogen-containing protonated base, by reacting sulfur with the corresponding diester of phosphorous acid, monoester of phosphornous acid or phosphinous acid of the formula (R)(R')PH(O)

the improvement which comprises effecting the reaction in the presence of an aqueous solution of an auxiliary base.

2. A process according to claim 1, wherein the auxiliary base used is a hydroxide of an alkali metal or alkaline earth metal, a nitrogen-containing inorganic base or an organic derivative of a nitrogen-containing base.

3. A process according to claim 1, wherein the aqueous solution has a concentration of 5–60%.

4. A process according to claim 1, wherein an excess of sulphur is used with respect to the phosphorus compound.

5. A process according to claim 4, wherein, after the reaction, excess sulphur is filtered off.

6. A process according to claim 1, wherein an excess of auxiliary base is used with respect to the phosphorus compound.

7. A process according to claim 6, wherein the auxiliary base comprises ammonia or trimethylamine and, after the reaction is complete, an inorganic acid is added to convert the salt form of the thioacid to the free acid.

8. A process according to claim 6, wherein the auxiliary base is ammonia and it and the sulphur are used in excess with respect to the phosphorus compound.

9. A process according to claim 1, wherein the temperature during reaction is about 0° to 60° C.

10. A process according to claim 1, wherein about 1 mol of di(2-ethylhexyl)phosphite is reacted with about 1.25 to 1.5 mols of sulphur and about 1.1 to 1.25 mols of an auxiliary base in an aqueous solution at a temperature between about 35° and 43° C.

11. A process according to claim 10, wherein the auxiliary base is aqueous ammonia or an aqueous trimethylamine solution.

* * * * *

UNITED STATES PATENT AND TRADEMARK OFFICE
CERTIFICATE OF CORRECTION

PATENT NO.  : 5,641,888
DATED       : June 24, 1997
INVENTOR(S) : Holzner, et al.

It is certified that error appears in the above-indentified patent and that said Letters Patent is hereby corrected as shown below:

Col. 6, line 46    Delete " phosphornous " and substitute
                   -- phosphonous --

Signed and Sealed this

Thirtieth Day of December, 1997

Attest:

BRUCE LEHMAN

Attesting Officer

Commissioner of Patents and Trademarks

REEXAMINATION CERTIFICATE (3753rd)

United States Patent [19]

Holzner et al.

[11] B1 5,641,888
[45] Certificate Issued Mar. 16, 1999

[54] SYNTHESIS OF AN O,O'-DIESTERS OF THIOPHOSPHORIC ACID, AN O-ESTER OF THIOPHOSPHONIC ACID, OR A THIOPHOSPHINIC ACID

[75] Inventors: Christoph Holzner; Ottfried Schlak, both of Köln; Rosemarie Grizan; Johannes Jezierski, both of Leverkusen, all of Germany

[73] Assignee: Bayer AG, Leverkusen, Germany

Reexamination Request:
No. 90/004,893, Jan. 14, 1998

Reexamination Certificate for:
Patent No.: 5,641,888
Issued: Jun. 24, 1997
Appl. No.: 588,479
Filed: Jan. 18, 1996

Certificate of Correction issued Dec. 30, 1997.

[30] Foreign Application Priority Data

Jan. 25, 1995 [DE] Germany .................. 195 02 197.5

[51] Int. Cl.$^6$ ..................................................... C07F 9/165
[52] U.S. Cl. .................. 558/123; 558/132; 562/8
[58] Field of Search ............................ 558/123, 132; 562/8

[56] References Cited

U.S. PATENT DOCUMENTS 2,862,016  11/1958  Sellmann .
3,294,874  12/1966  Schrader .
4,416,834  11/1983  Feyen et al. .................. 558/132 X
4,555,368  11/1985  Robertson .

FOREIGN PATENT DOCUMENTS 835 145    11/1949  Germany .
10 50 330  2/1959   Germany .
75-160221  12/1975  Japan .

OTHER PUBLICATIONS

Phosphorus, Sulfur, and Silicon, 1991 vol. 63, pp. 315–322 "Synthesis and Tribochemical Behavior of Some Monothiophosphoric Acid Derivatives" Ciba Geigy Marienberg GMBH, Germany.

Chemical Abstracts, vol. 084, No. 21, May 24, 1976, "Monothiophosphoric Acid Diester Alkaline Earth Metal Salts".

Chemical Abstracts, vol. 089, No. 25, Dec. 18, 1978, "Synthesis of Dioctylthiophosphoninic and Dioctylythiophosphoric Acids".

Chemical Abstracts, vol. 119, No. 3, Jul. 19, 1993, "Synthesis of di(2-ethylhexyl)thiophosphoric Acid".

Houben–Weyl, "Methoden der Organischen Chemie", 4th Edition, vol. 12/2, pp. 7–8.

*Primary Examiner*—Michael G. Ambrose

[57] ABSTRACT

Preparing O,O'-diesters of thiophosphoric acid, O-monoesters of thiophosphonic acid or thiophosphinic acids and their salts, from diesters of phosphorous acid, monoesters of phosphorous acids or phosphinous acids and sulphur in the presence of an aqueous solution of an auxiliary base. The solution can be used in further syntheses or as extraction agent for cations.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–11, dependent on an amended claim, is determined to be patentable.

New claim 12 is added and determined to be patentable.

1. In the preparation of an O,O'-diester of thiophosphoric acid[, an O-monoester of thiophosphonic acid or a thiophosphinic acid] of the formula

[(R)(R')PS(OH)] $(R_1O)(R_1'O)PS(OH)$ or a salt thereof of the formula

[(R)(R')PS(OZ)] $(R_1O)PS(OZ)$ wherein

[R] $R_1$ and [R'] $R_1'$ each independently is an alkyl, alkenyl, cycloalkyl or aryl group with 1 to 18 carbon atoms, whose hydrogen atoms may be replaced completely or partly by halogen atoms or by neutral or basic groups; [or $R_1O$ or $R_1'O$ group in which R' and $R_1'$ each independently has the same meaning as R and R'.] and Z is an alkali metal ion, alkaline earth metal ion, protonated nitrogen-containing inorganic base or organic derivative of a nitrogen-containing protonated base, by reacting sulfur with the corresponding diester of phosphorous acid[, monoester of phosphornous acid or phosphinous acid] of the formula

[(R)(R')PH(O)] $(R_1O)$ $(R_1'O)PH(O)$ the improvement which comprises effecting the reaction in the presence of an aqueous solution of an auxiliary base.

*12. A process according to claim 9, wherein the temperature during reaction is about 0° to 43° C.*

\* \* \* \* \*